US011123392B2

(12) United States Patent
Zhu et al.

(10) Patent No.: US 11,123,392 B2
(45) Date of Patent: Sep. 21, 2021

(54) TRADITIONAL CHINESE MEDICINE COMPOSITION FOR TREATING INTERSTITIAL PULMONARY FIBROSIS AND METHOD FOR MAKING SAME

(71) Applicant: Jiangsu Traditional Chinese Medicine Research Institute, Jiangsu (CN)

(72) Inventors: Qiyong Zhu, Jiangsu (CN); Qingling Xiao, Jiangsu (CN); Xiaoli Chen, Jiangsu (CN); Yeqing Zhang, Jiangsu (CN); Jianming Ju, Jiangsu (CN)

(73) Assignee: Jiangsu Traditional Chinese Medicine Research Institute, Nanjing (CN)

( * ) Notice: Subject to any disclaimer, the term of this patent is extended or adjusted under 35 U.S.C. 154(b) by 33 days.

(21) Appl. No.: 16/729,333

(22) Filed: Dec. 28, 2019

(65) Prior Publication Data

US 2020/0297793 A1 Sep. 24, 2020

(30) Foreign Application Priority Data

Mar. 19, 2019 (CN) ......................... 201910208416.5

(51) Int. Cl.

| | |
|---|---|
| ***A61K 36/537*** | (2006.01) |
| ***A61K 36/736*** | (2006.01) |
| ***A61K 35/62*** | (2006.01) |
| ***A61P 11/00*** | (2006.01) |
| ***A61K 36/88*** | (2006.01) |
| ***A61K 36/185*** | (2006.01) |
| ***A61K 36/65*** | (2006.01) |

(52) U.S. Cl.
CPC ............ *A61K 36/537* (2013.01); *A61K 35/62* (2013.01); *A61K 36/185* (2013.01); *A61K 36/65* (2013.01); *A61K 36/736* (2013.01); *A61K 36/88* (2013.01); *A61P 11/00* (2018.01)

(58) Field of Classification Search
None
See application file for complete search history.

(56) References Cited

FOREIGN PATENT DOCUMENTS

| | | | |
|---|---|---|---|
| CN | 103599356 A | | 2/2014 |
| CN | 106266936 A | * | 1/2017 |
| CN | 107596110 A | | 1/2018 |

OTHER PUBLICATIONS

Zhang, Y. et al. Traditional Chinese Medicine Combined with Pulmonary Drug Delivery System and Idiopathic Pulmonary Fibrosis. Biomedicine & Pharmacotherapy 133:1-11, Jan. 2021. (Year: 2021).*

* cited by examiner

*Primary Examiner* — Ralph J Gitomer

(57) ABSTRACT

Disclosed herein is a traditional Chinese medicine composition for treating interstitial pulmonary fibrosis, which is prepared from 10-20 parts by weight of Radix salviae miltiorrhiza, 4-8 parts by weight of peach kernel, 2-4 parts by weight of hirudo, 5-15 parts by weight of Radix paeoniae rubra, 5-15 parts by weight of Radix ophiopogonis, 5-15 parts by weight of Chebulae fructus immaturus and 2-4 parts by weight of *Oroxylum indicum* (Linn.) Kurz. The invention also provides a method of preparing the composition.

3 Claims, No Drawings

TRADITIONAL CHINESE MEDICINE COMPOSITION FOR TREATING INTERSTITIAL PULMONARY FIBROSIS AND METHOD FOR MAKING SAME

CROSS-REFERENCE TO RELATED APPLICATIONS

This application is claims the benefit of priority from Chinese Patent Application No. 201910208416.5, filed on Mar. 19, 2019. The content of the aforementioned application, including any intervening amendments thereto, is incorporated herein by reference.

TECHNICAL FIELD

This application relates to traditional Chinese medicines, and more particularly to a traditional Chinese medicine composition for treating interstitial pulmonary fibrosis and a method of making the same.

BACKGROUND

The interstitial pulmonary fibrosis is derived from various interstitial lung diseases, and has complex pathogeny. It has been demonstrated by modern medical research that the pathogeny is associated with the inhaled dusts, toxic gases and environmental pollutants and genetic factors. Moreover, the interstitial pulmonary fibrosis may also be secondary to respiratory diseases, immune system diseases and the excessive use of some drugs such as chemotherapy drugs. The interstitial pulmonary fibrosis is one of the most frequent respiratory diseases since it may be caused by chronic obstructive pulmonary disease, bronchial asthma, interstitial pneumonia, radiation pneumonia and pulmonary damage caused by rheumatic immune system diseases. This disease is mainly characterized by progressive dyspnea, dry cough and wheezing after the physical activity, and is often aggravated due to repeated infections. Currently, there is no western medicine for effectively treating the interstitial pulmonary fibrosis except the use of glucocorticoid. However, the glucocorticoid is actually not very suitable for the treatment due to the uncertain efficacy and numerous side effects. The interstitial pulmonary fibrosis will be aggravated by repeated deferment, and involves poor prognosis, making it difficult to be completely treated.

SUMMARY

An object of this application is to provide a traditional Chinese medicine composition for treating interstitial pulmonary fibrosis and a method of making the same.

The technical solutions of this application are described as follows.

In a first aspect, this application provides a traditional Chinese medicine composition for treating interstitial pulmonary fibrosis, wherein the composition is prepared from 10-20 parts by weight of Radix salviae miltiorrhiza, 4-8 parts by weight of peach kernel, 2-4 parts by weight of hirudo, 5-15 parts by weight of Radix paeoniae rubra, 5-15 parts by weight of Radix ophiopogonis, 5-15 parts by weight of Chebulae fructus immaturus and 2-4 parts by weight of *Oroxylum indicum* (Linn.) Kurz.

In an embodiment, the composition is prepared from 15 parts by weight of Radix salviae miltiorrhiza, 6 parts by weight of peach kernel, 3 parts by weight of hirudo, 10 parts by weight of Radix paeoniae rubra, 10 parts by weight of Radix ophiopogonis, 10 parts by weight of Chebulae fructus immaturus and 3 parts by weight of *Oroxylum indicum* (Linn.) Kurz.

In a second aspect, this application provides a method of preparing the above medicine composition, comprising:

mixing Radix salviae miltiorrhiza, peach kernel, hirudo, Radix paeoniae rubra, Radix ophiopogonis, Chebulae fructus immaturus and *Oroxylum indicum* (Linn.) Kurz in a mass ratio of 10-20: 4-8: 2-4: 5-15: 5-15: 5-15: 2-4; extracting the reaction mixture by decoction with water in a mass ratio of 1:10 for 2 h to collect a first extract; extracting the reaction mixture again by decoction with water in a mass ratio of 1:8 for 2 h to collect a second extract; combining the first extract with the second extract; filtering the combined extract; concentrating the filtrate under vacuum to produce a paste with a relative density of 1.15 at 60° C.; drying the paste under vacuum followed by pulverization to produce dried powder; and mixing the dried powder with dextrin and stevioside uniformly followed by granulation and drying to produce the composition.

In a third aspect, this application further provides a method of treating interstitial pulmonary fibrosis in a patient in need thereof, comprising: administering an effective amount of the composition of claim 1 to the patient.

All the medicinal materials used herein are in compliance with the pharmacopoeia standards.

The beneficial effects of the invention are described as follows.

The interstitial pulmonary fibrosis is mainly characterized by deficiency in origin and enrichment in symptom. From the point of view of the deficiency in origin, the consumptive lung disease indicates that the lung is too weak to work well, causing the deficiency of qi and blood and the "Luoxu Burong". From the point of view of the enrichment in symptom, the pulmonary arthralgia indicates that the lung suffers from arthralgia, causing the obstruction of qi and blood and the stasis and obstruction of vessel and collateral. The above two respectively show the pathogenesis characteristics of pulmonary interstitial fibrosis at different stages. In the early stage, the lung and kidney are deficient, and the invasion of exogenous pathogenic factors repeatedly occurs, failing to completely eliminate the pathogens and obstructing the diffusion of lung qi. Vessels are converged in the lung and the lung governs coordinative activities of viscera. Once suddenly exposing to warm-heat pathogen and poison, the fluid and qi in the lung are damaged thereby, which results in obstruction in the lung collaterals, so that the lung fails to govern coordinative activities of viscera. Therefore, qi fails to command the blood and promote the fluid circulation, and the stagnation of blood will lead to the formation of stasis and the stagnation of fluid will lead to the formation of phlegm. When the lung qi fails to be applied to the heart blood, it is easy to cause irritability and insomnia. Moreover, a disturbance in ascending and descending is observed in lung and spleen, which causes reverse restriction to the vital organ, causing the qi to fail to promote the blood production and resulting in interior exhaustion of primordial qi and qi stagnation and blood stasis. Given the above, the interstitial pulmonary fibrosis is commonly characterized by dry cough, less sputum, asthma, chest tightness and red tongue together with purple air in clinic. Professor Zhu Qiyong, as one of the fifth batch of instructors for the inheritance of academic experience of the national traditional Chinese medicine experts, has worked in medicine for more than years and has rich knowledge and experience. Prof. Zhu has undertaken numerous research projects, and presided over the research on new respiratory medicines such as lung-heart tablets, Qingjin Granules, Anchuan tablets, tablets for treating Pulmonary Emphysema, Feishu Capsules and tablets for treating Pharyngitis. According to the rich clinical experience for the treatment of pulmonary interstitial fibrosis, Prof. Zhu has concluded that the pulmonary interstitial fibrosis is mainly characterized by stasis and stagnation, so that it is required to promote blood circulation and remove blood stasis, moreover, the lung and kidney should also be simultaneously invigorated. The pulmonary interstitial fibrosis has the characteristics of simultaneous presence of sthenia and asthenias in the chronic deferment stage, so that the purgation-tonifying therapy predominated by tonifying should be performed in the practical treatment. The principle of slowly treating the chronic disease is introduced into the tonifying to completely remove the evils, restoring the functions of lung and kidney. The combination of promotion of blood circulation and nourishing of yin often has better clinical effect than the alone use thereof. At the same time, the pulmonary interstitial fibrosis often involves the throat. As recited in "Jade Key to the Secluded Chamber" ("Chonglou Yuyao") that "the throat is hollow to allow the breath to come in and out and pertains to the pulmonary system to plays a role as the passage of the lung qi", the repeated occurrence of dryness, pain and itch to the throat will the disease more difficult to heal. Therefore, the pulmonary interstitial fibrosis is often clinically treated through the combination with the Qingfei Liyan treatment. Based on the above, Prof. Zhu believes that the pathogenesis of pulmonary interstitial fibrosis is substantially characterized by yin deficiency and blood stasis, so that the promotion of blood circulation, nourishing of yin and relieving of sore-throat should be performed throughout the treatment.

Based on the above understanding of the etiology and pathogenesis, the invention employs Radix salviae miltiorrhiza as monarch drug; peach kernel, hirudo and Radix paeoniae rubra as ministerial drugs; Radix ophiopogonis as adjuvant drug; and Chebulae fructus immaturus and *Oroxylum indicum* (Linn.) Kurz as envoy drugs, which facilitates the nourishing of yin and removal of blood stasis, so that compared to the alone use of the conventional treatment, the patient suffering from the interstitial pulmonary fibrosis may be more significantly improved in arterial blood qi, pulmonary function, symptom scores in the additional use the composition provided herein. The invention has achieved good efficacy in clinical practice.

The Radix salviae miltiorrhiza used herein is bitter in taste and slightly cold in nature, and has heart, pericardium and liver meridian tropism. It plays a role in promoting blood circulation, regulating the menstruation, removing the stasis and relieving the pain. Moreover, it has been demonstrated that the Radix salviae miltiorrhiza water decoction is able to effectively inhibit the increase of the mice with pulmonary fibrosis in lung index and transforming growth factor in lung tissue, inhibiting the pulmonary fibrosis. The peach kernel and Radix paeoniae rubra are bitter in taste and has a liver meridian tropism. They play a role in cooling blood, promoting the blood circulation, dispersing blood stasis and relieving the pain, so that they are commonly used together in drugs for treating various types of congestion and blockage, such as in Taohong Siwu Decoction to treat congestion, amenorrhea and dysmenorrheal; in Guizhi Fulin pills to treat the abdominal lumps caused by long-term stasis; and in Polygonum cuspidatum powder to treat the pain caused by ecchymoma. As recited by Zhang Xichun that "the drugs for removing stasis often hurt the vital qi, while hirudo, salty in taste, can be used to remove the stasis without damaging the vital qi, so the hirudo is used herein to enhance the efficacy. In addition, it has further been reported by Sheng Li that the hirudo can reduce the collagen content of lung tissue and lower the degree of pulmonary fibrosis. Dai Lingjuan et al. have found that ligustrazine, a traditional Chinese medicine for promoting blood circulation and removing blood stasis, can significantly relieve the alveolitis and pulmonary fibrosis in rats when compared to the control group. The Radix ophiopogonis, sweet and slightly bitter in taste, has a lung, stomach and heart meridian tropism, and plays a role in nourishing lung yin and clearing lung heat, so that it is suitable for the dry cough, less phlegm, dryness in nose and throat and pharyngalgia caused by yin deficiency and lung dryness. It has been mentioned in Bencao Huiyan that the Qingxin Runfei drugs can treat the lung heat and dryness, consecutive cough, pulmonary collapse, shortness of breath, dyspnea of deficiency type and lung fire. The Chebulae fructus immaturus and *Oroxylum indicum* (Linn.) Kurz have lung meridian tropism, and play a role in clearing lung heat, relieving sore-throat, dissolving phlegm and suppressing cough.

DETAILED DESCRIPTION OF EMBODIMENTS

The invention will be further described in detail below with reference to the embodiments, and these embodiments are not intended to limit the invention. Any modifications, changes and replacements made without departing from the spirit of the invention should fall within the scope of the invention.

Example 1

Radix salviae miltiorrhiza, peach kernel, hirudo, Radix paeoniae rubra, Radix ophiopogonis, Chebulae fructus immaturus and *Oroxylum indicum* (Linn.) Kurz were mixed in a mass ratio of 15:6:3:10:10:10:3 and extracted with water by decoction in a mass ratio 1:10 for 2 h to collect a first extract. Then the reaction mixture was extracted again with water by decoction in a mass ratio of 1:8 for 2 h to collect a second extract. The first extract and the second extract were combined and filtered. The filtrate was concentrated under vacuum to produce a paste with a relative density of 1.15 at 60° C. The paste was dried under vacuum, pulverized, mixed with dextrin and stevioside uniformly, granulated and dried to produce a medicine composition for treating interstitial pulmonary fibrosis.

Example 2

Radix salviae miltiorrhiza, peach kernel, hirudo, Radix paeoniae rubra, Radix ophiopogonis, Chebulae fructus immaturus and *Oroxylum indicum* (Linn.) Kurz were mixed in a mass ratio of 10:8:2:15:5:15:2 and extracted with water by decoction in a mass ratio 1:10 for 2 h to collect a first extract. Then the reaction mixture was extracted again with water by decoction in a mass ratio of 1:8 for 2 h to collect a second extract. The first extract and the second extract were combined and filtered. The filtrate was concentrated under vacuum to produce a paste with a relative density of 1.15 at 60° C. The paste was dried under vacuum, pulverized, mixed with dextrin and stevioside uniformly, granulated and dried to produce a medicine composition for treating interstitial pulmonary fibrosis.

Example 3

Radix salviae miltiorrhiza, peach kernel, hirudo, Radix paeoniae rubra, Radix ophiopogonis, Chebulae fructus immaturus and *Oroxylum indicum* (Linn.) Kurz were mixed in a mass ratio of 20:4:4:5:15:5:4 and extracted with water by decoction in a mass ratio 1:10 for 2 h to collect a first extract. Then the reaction mixture was extracted again with water by decoction in a mass ratio of 1:8 for 2 h to collect a second extract. The first extract and the second extract were combined and filtered. The filtrate was concentrated under vacuum to produce a paste with a relative density of 1.15 at 60° C. The paste was dried under vacuum, pulverized, mixed with dextrin and stevioside uniformly, granulated and dried to produce a medicine composition for treating interstitial pulmonary fibrosis.

Example 4

Clinical Experiment 40 cases suffering from acutely-exacerbated interstitial pulmonary fibrosis were selected for clinical observation in 2016-2018. All patients were routinely treated with glucocorticoid and an inhaled bronchodilator, and patients in the treatment group were further treated with the composition prepared in Example 1 (Feixian Formula). After treated for 3 weeks, the patients were evaluated through the traditional Chinese medicine symptom complex score, where the score standards were shown in Table 1 and the results were shown in Table 2. It can be seen from Table 2 that the symptom complex scores of the treatment group were all higher than those of the control group. Moreover, the patients treated with the Feixian Formula were clinically observed to be correspondingly improved in the objective indexes (as shown in Table 3).

The clinical test was performed as follows.

1. Diagnostic Criteria 1.1 Western Medicine Diagnostic Criteria

Interstitial pulmonary fibrosis was derived from various etiological factors, including primary interstitial pulmonary fibrosis and secondary interstitial pulmonary fibrosis. The chest HRCT showed the change of the interstitial pulmonary fibrosis, and Veclro rale can be diagnosed by lung auscultation. Moreover, the acropachy was present or absent. The pulmonary function test showed the restricted ventilation function disturbance.

The appropriate patients were required to involve the clinical manifestations of aggravated cough, chest tightness and asthma.

1.2 Traditional Chinese Medicine Syndrome Diagnostic Criteria

The syndrome of yin deficiency and blood stasis was mainly characterized by: repeated cough predominated by dry cough; afternoon tidal fever; dysphoria with feverish sensation in chest; mouth and throat dryness; local tingling; cough with shortness of breath and chest tightness; red tongue with dark purple air or tongue spots; thready and uneven pulse or thready and rapid pulse.

2. Selection Criteria 2.1 Inclusion Criteria (1) 18-75 years old;

(2) Meeting the Western medicine diagnostic criteria for interstitial pulmonary fibrosis and being in the acute exacerbation stage;

(3) Meeting the traditional Chinese medicine syndrome diagnostic criteria for yin deficiency and blood stasis; and (4) Being informed; voluntarily agreeing to receive the treatment; and signing an informed consent form.

Any one complying the above 4 criteria can be included in the cases.

2.2 Exclusion Criteria (1) Under 18 or over 75; pregnant or lactating women; and allergic to this medicine;

(2) Suffering from severe primary diseases such as diabetes, liver, kidney, brain and hematopoietic diseases, or mental illness; and (3) Failing to meet the inclusion criteria; failing to take the medicine as prescribed; failing to determine the efficacy or safety.

2.3 Case Exclusion and Dropping-Out and Trial Suspension

Doctors participating in clinical trials should carefully record the reasons for the exclusion, dropping-out and suspension, the relationship with the trial and the evaluation at the time of suspension. The withdrawal depending on the organizer was defined as exclusion, while the withdrawal depending on the subject was defined as dropping-out. The specific regulations were described as follows:

(1) Subjects with poor compliance; failing to take the drug as prescribed; or involving an efficacy failing to be determined or incomplete data to affect the judgment of efficacy and safety, should be excluded.

(2) Subjects involving serious adverse event; involving complications or special physiological changes; or unsuitable for the subsequent test, should be excluded.

(3) Subjects involving insignificant therapeutic effect; failing to participate in the subsequent clinical trial for some reasons such as adverse event or fear; or withdrawing without any reason, are deemed to be dropped out.

(4) In the case that during the trial, serious safety problem occurs or the drug is observed to be not good enough in efficacy or to be ineffective, the trial may be suspended.

3. Case Source and Grouping 40 cases were selected from outpatient and inpatients in the Traditional and Western Medicine Hospital in Jiangsu, and randomly and averagely divided into two groups, i.e., the treatment group and the control group.

4. Trial 4.1 Drug Administration

The treatment group and the control group were both routinely treated with western medicines including glucocorticoids, expectorants and inhaled bronchodilators. Moreover, the treatment group was further treated with the Fuxian Formula prepared in Example 1.

4.2 Observation

The medication was observed for 1 month, and the follow-up was performed once respectively before and after the observation. Moreover, the follow-up was also performed once respectively on the $3^{rd}$, $7^{th}$ and $14^{th}$ day of the course, and the conditions were recorded on the TCM symptom score table. Except for those suffering from serious adverse reactions, the follow-up was generally not performed any more after the observation period. Those suffering from serious adverse reactions or involving obvious abnormal values in the safety examination should be followed up or re-examined for the abnormal items.

4.3 Indexes and Recording Method (1) Safety Observation

The observation for the safety was performed once respectively at the beginning and end of the course.

1-1 General physical examination items: body temperature, breathing, pulse and blood pressure;

1-2 Routine tests for blood, urine and stool;

1-3 ECG, liver function (ALT), renal function (BUN, Cr).

(2) Therapeutic Effect Observation 2-1 TCM syndromes and scores: TCM symptoms (including cough, asthma, shortness of breath, cyanosis); physical signs (tongue and pulse); calculation of the scores before and after treatment; changes of the total syndrome score.

2-2 Effect on the objective indexes

Examination for the lung function FVC and DLCO was performed respectively before and after the treatment.

4.4 Clinical Efficacy Evaluation Index

The standard of TCM syndrome efficacy is evaluated according to the guidelines for clinical research of new Chinese medicines and actual conditions.

TABLE 1

TCM Syndrome Scoring Standards for Pulmonary Interstitial Fibrosis

| Symp- | | Items | | | |
|---|---|---|---|---|---|
| toms | Score | 0 | 2 | 4 | 6 |
| Cough | | No | Slight cough without affecting the daily life | Moderate cough, coughing during the day or night, tolerable | Frequently coughing, intolerable |
| Cyanosis | | No | Occurring after strenuous activities | Occurring after the activity and disappearing after a rest | Occurring any time |
| Asthma or shortness of breath | | No | Occurring occasionally after strenuous activities without affecting life | Occurring during most daily activities, but absent during a rest | Occurring any time |
| Frequency of cough | | No | 1-5 times one day, each within 2 min | 5-10 times one day, each for 2-5 min | More than 10 times one day, each for more than 5 min |
| Fatigue | | No | Slight metal fatigue | Metal fatigue | Extreme metal fatigue |

4.5 Evaluation Method

Yin deficiency and blood stasis syndrome caused by interstitial pulmonary fibrosis was evaluated and scored according to the following formula:

(Symptom score before treatment−Symptom score after treatment)÷Symptom score before treatment×100%.

(1) Clinical control: clinical symptoms and signs disappeared or basically disappeared, and syndrome score were decreased by 95% or more;

(2) Significant effect: clinical symptoms and signs were improved significantly, and syndrome scores were reduced by 70%-95%;

(3) General effect: clinical symptoms and signs were improved, and syndrome scores were decreased by 30%-70%;

(4) Free of effect: clinical symptoms and signs were not improved significantly, or even worsened, and the syndrome scores were decreased by 0%-30%.

4.6 Data Processing and Statistical Analysis

The data processing and statistical analysis were performed using SPSS 19.0, and the results were represented by mean±SD. The comparison between the two groups was made by t test, and the comparison between the group before and after the treatment was performed using paired t test. $P<0.05$ indicated that the difference was of statistical significance.

5. Results 5.1 Safety Index

The blood, urine, stool routine test, electrocardiogram, liver function (ALT), and renal function (BUN, Cr) indexes of the treatment group before and after the observation all did not show clinical abnormalities, demonstrating that the invention had excellent safety.

5.2 Therapeutic Indexes

It can be seen from Table 2 that the treatment group was superior to the control group both in the scores of the symptoms and signs. As shown in Table 3, the patients who treated with the Feixian Formula were clinically observed to be accordingly improved in the lung function indexes such as FVC and DLCO.

TABLE 2

| Comparison of clinical efficacies for the two groups before and after the treatment | | | | | |
|---|---|---|---|---|---|
| Group | n | Significant effect (cases)/(%) | General effect (cases)/(%) | Free of effect (cases)/(%) | Total effective cases and rates (%) |
| Treatment group | 20 | 12 (60.00) | 8 (40.00) | 0 (0) | 20 (100.00) |
| Control group | 20 | 10 (50.00) | 8 (40.00) | 2 (10.00) | 18 (90.00) |

It can be seen from Table 2 that the treatments respectively for the two groups had significant clinical efficacy, and the therapeutic effect on the treatment group was better than that of the control group.

TABLE 3

| Comparison of lung function indexes between two groups before and after treatment | | | |
|---|---|---|---|
| Group | | PVC (L) | DLCO (mL · $mmHg^{-1} \cdot min^{-1}$) |
| Treatment group (n = 20) | Before | 1.58 ± 0.23 | 45.1 ± 10.6 |
| | After | 1.86 ± 0.43 | 59.2 ± 11.4 |
| Control group (n = 20) | Before | 1.61 ± 0.21 | 44.2 ± 10.2 |
| | After | 1.77 ± 0.23 | 52.2 ± 13.1 |

Notes:
the comparisons were performed using t test at $P < 0.05$.

It is apparent that the above embodiments are merely illustrative of the invention, and are not intended to limit the invention. Various modifications, variations and replacements made by those skilled in the art without departing from the spirit of the invention should fall within the scope of the invention.

What is claimed is:

1. A composition for treating interstitial pulmonary fibrosis, wherein the composition comprises 10-20 parts by weight of Radix salviae miltiorrhizae, 4-8 parts by weight of peach kernel, 2-4 parts by weight of hirudo, 5-15 parts by weight of Radix paeoniae rubra, 5-15 parts by weight of Radix ophiopogonis, 5-15 parts by weight of Chebulae fructus immaturus and 2-4 parts by weight of *Oroxylum indicum* (Linn.) Kurz.

2. The composition of claim 1, wherein the composition comprises 15 parts by weight of Radix salviae miltiorrhizae, 6 parts by weight of peach kernel, 3 parts by weight of hirudo, 10 parts by weight of Radix paeoniae rubra, 10 parts by weight of Radix ophiopogonis, 10 parts by weight of Chebulae fructus immaturus and 3 parts by weight of *Oroxylum indicum* (Linn.) Kurz.

3. A method of treating interstitial pulmonary fibrosis in a patient in need thereof, comprising:

administering an effective amount of the composition of claim 1 to the patient.

* * * * *